US010869652B2

(12) United States Patent
Carpenter et al.

(10) Patent No.: US 10,869,652 B2
(45) Date of Patent: Dec. 22, 2020

(54) ANALOGUE TIME DIVISION MULTIPLEXING FOR CABLE REDUCTION IN IMAGING CATHETERS

(71) Applicants: GEORGIA TECH RESEARCH CORPORATION, Atlanta, GA (US); University of Leeds, Yorkshire (GB)

(72) Inventors: Thomas Carpenter, Leeds (GB); M. Wasequr Rashid, Atlanta, GA (US); F. Levent Degertekin, Atlanta, GA (US); Steven Freear, Leeds (GB); David Matthew Joseph Cowell, Leeds (GB)

(73) Assignees: Georgia Tech Research Corporation, Atlanta, GA (US); University of Leeds, Leeds (GB)

( * ) Notice: Subject to any disclaimer, the term of this patent is extended or adjusted under 35 U.S.C. 154(b) by 300 days.

(21) Appl. No.: 15/768,435

(22) PCT Filed: Oct. 14, 2016

(86) PCT No.: PCT/US2016/057034
§ 371 (c)(1),
(2) Date: Apr. 13, 2018

(87) PCT Pub. No.: WO2017/066564
PCT Pub. Date: Apr. 20, 2017

(65) Prior Publication Data
US 2018/0317889 A1    Nov. 8, 2018

Related U.S. Application Data

(60) Provisional application No. 62/241,927, filed on Oct. 15, 2015.

(51) Int. Cl.
*A61B 8/00*      (2006.01)
*A61B 8/12*      (2006.01)
(Continued)

(52) U.S. Cl.
CPC ............ *A61B 8/56* (2013.01); *A61B 8/12* (2013.01); *A61B 8/4488* (2013.01);
(Continued)

(58) Field of Classification Search
USPC ............................................ 367/7
See application file for complete search history.

(56) References Cited

U.S. PATENT DOCUMENTS 5,229,933 A    7/1993   Larson
6,130,920 A *  10/2000  Powell, II ............. H04L 7/0062
                                                    375/343
(Continued)

FOREIGN PATENT DOCUMENTS

WO    2015/048321    4/2015

OTHER PUBLICATIONS

Search Report and Opinion from PCT Application No. PCT/US16/057034 dated Dec. 28, 2016 (16 pages).

*Primary Examiner* — James R Hulka
(74) *Attorney, Agent, or Firm* — Troutman Pepper Hamilton Sanders LLP; Ryan Schneider; Mark Jones

(57) ABSTRACT

The disclosed technology relates to imaging catheters. A method is provided that includes: receiving, from a plurality of transducers disposed on a catheter probe, a corresponding plurality of analog signals; selectively sampling the plurality of analog signals; multiplexing to produce a sequence of samples; and transmitting the sequence of samples to a receiver circuit. The receiver circuit includes a clock; an analog to digital converter (ADC) in communication with the clock; and a sampling phase correction circuit in communication with the clock and the ADC. The method further includes: determining optimum sampling times based on measured signal delays associated with the system; adjusting a phase of the clock based on the measured signal delays;
(Continued)

'm' = Number of Channels in TDM
'f' = Sample Rate per channel and communicating the phase-adjusted clock to the transmitter circuit for the selective sampling of the analog signals. Certain embodiments of the disclosed technology may further be utilized in conjunction with beamforming.

28 Claims, 7 Drawing Sheets

(51) Int. Cl.
  *G01S 7/52* (2006.01)
  *G01S 15/89* (2006.01)
  *G10K 11/34* (2006.01)
  *A61B 8/08* (2006.01)
  *A61B 5/055* (2006.01)
  *A61B 5/0402* (2006.01)

(52) U.S. Cl.
  CPC .............. *A61B 8/5207* (2013.01); *A61B 8/58* (2013.01); *G01S 7/5208* (2013.01); *G01S 7/52022* (2013.01); *G01S 7/52025* (2013.01); *G01S 7/52034* (2013.01); *G01S 7/52077* (2013.01); *G01S 7/52087* (2013.01); *G01S 7/52095* (2013.01); *G01S 15/8915* (2013.01); *G10K 11/346* (2013.01); *A61B 5/0402* (2013.01); *A61B 5/055* (2013.01); *G01S 7/52079* (2013.01)

(56) References Cited

U.S. PATENT DOCUMENTS

| | | | | |
|---|---|---|---|---|
| 7,257,439 | B2 * | 8/2007 | Llinas | A61B 5/04001 600/544 |
| 8,345,731 | B2 * | 1/2013 | Jin | H03M 1/1255 342/108 |
| 8,792,590 | B2 * | 7/2014 | Furman | H04L 25/06 341/118 |
| 8,837,557 | B2 * | 9/2014 | Jin | H03M 1/1255 375/134 |
| 8,891,334 | B2 * | 11/2014 | Degertekin | G01S 15/8993 367/137 |
| 9,259,206 | B2 * | 2/2016 | Degertekin | A61B 8/12 |
| 9,289,132 | B2 * | 3/2016 | Ghaffari | A61B 5/01 |
| 2004/0133118 | A1 | 7/2004 | Llinas | |
| 2007/0213616 | A1 * | 9/2007 | Anderson | A61B 8/445 600/448 |
| 2010/0087782 | A1 | 4/2010 | Ghaffari et al. | |
| 2010/0215125 | A1 | 8/2010 | Furman | |
| 2013/0064043 | A1 * | 3/2013 | Degertekin | G01S 15/8925 367/137 |
| 2013/0094540 | A1 | 4/2013 | Jin | |
| 2014/0236017 | A1 | 8/2014 | Degertekin et al. | |
| 2016/0245670 | A1 * | 8/2016 | Nelson | G01D 5/2066 |

* cited by examiner

ANALOGUE TIME DIVISION MULTIPLEXING FOR CABLE REDUCTION IN IMAGING CATHETERS

CROSS REFERENCE TO RELATED APPLICATION

This application claims priority under 35 U.S.C. 119 to U.S. Provisional Patent Application No. 62/241,927 entitled "Analogue Time Division Multiplexing for Cable Reduction in Imaging Catheters," filed 15 Oct. 2015, the contents of which are incorporated by reference in their entirety as if fully set forth herein.

STATEMENT REGARDING FEDERALLY SPONSORED RESEARCH OR DEVELOPMENT

This invention was made with government support under Grant No. U01-HL121838 awarded by the National Institute of Health. The government has certain rights in the invention.

FIELD OF THE DISCLOSED TECHNOLOGY

The disclosed technology generally relates to imaging catheters, and in particular, to methods and systems for reduction of cabling and associated electrical connections associated with the imaging catheters.

BACKGROUND

Imaging catheters can be utilized to provide images of tissues inside the body without the need for invasive surgery. In applications requiring high resolution or 3D images, multiple transducer elements may be utilized to simultaneously capture a pulse echo response (for example, from a single ultrasonic pulse) and the multiple signals from the transducers may be utilized to form the image.

In real-time ultrasound imaging applications, catheters have size restrictions to enable safe passage through openings, channels, or cavities within in the body. Such size restrictions can limit the number (and associated bundle size) of cables that transfer the imaging signals from the transducers, through the cable bundle, and to external equipment. Furthermore, the length requirement for catheters and limited power available to on-chip cable drivers leads to limited signal strength at the receiver end. A need exists for improved systems and methods for reducing cable count and associated electrical connections associated with imaging catheters.

BRIEF SUMMARY

Some or all of the above needs may be addressed by certain embodiments of the disclosed technology.

Certain embodiments of the disclosed technology may include a system. The system can include an imaging array comprising a plurality of transducers disposed on at least a distal portion of a catheter probe, and a transmitter circuit disposed in the catheter probe. The transmitter circuit can include: a plurality of sample and hold circuits configured for selective sampling of analog signals received from the corresponding plurality of transducers; and a multiplexer in communication with the plurality of sample and hold circuits and configured for sequencing samples received from the plurality of sample and hold circuits. The system can include a receiver circuit in communication with the transmitter circuit. The receiver circuit may include: a clock; an analog to digital converter (ADC) in communication with the clock; and a sampling phase correction circuit in communication with the clock and the ADC. The sampling phase correction circuit is configured to: determine optimum sampling times based on measured signal delays associated with the system; adjust a phase of the clock based on the measured signal delays; and communicate the phase-adjusted clock to the transmitter circuit for the selective sampling of the analog signals by the plurality of sample and hold circuits.

According to another exemplary embodiment of the disclosed technology, a method is provided. The method includes: receiving, at a front end of a transmitter circuit disposed in a catheter probe, and from a plurality of transducers disposed on the catheter probe, a corresponding plurality of analog signals; selectively sampling, with at least one sample and hold circuit, the plurality of analog signals received from the corresponding plurality of transducers; multiplexing the selectively sampled analog signals to produce a sequence of samples; and transmitting the sequence of samples to a receiver circuit in communication with the transmitter circuit. The receiver circuit includes a clock; an analog to digital converter (ADC) in communication with the clock; and a sampling phase correction circuit in communication with the clock and the ADC. The method further includes: determining, with the sampling phase correction circuit, optimum sampling times based on measured signal delays associated with the system; adjusting a phase of the clock based on the measured signal delays; and communicating the phase-adjusted clock to the transmitter circuit for the selective sampling of the analog signals by the at least one sample and hold circuit.

According to another exemplary embodiment of the disclosed technology, a method is provided. The method includes: receiving, at a front end of a transmitter circuit disposed in a catheter probe, and from a plurality of transducers disposed on the catheter probe, a corresponding plurality of analog signals; and beamforming the received plurality of analog signals. The beamforming can include: controlling relative phases between respective signals of a group of transducer elements from the plurality of transducers; and combining the phase-controlled signals. The method can further include: sampling, with at least one sample and hold circuit, the beamformed signals; multiplexing the beamformed signals; and transmitting the multiplexed and beamformed signals to a receiver circuit in communication with the transmitter circuit.

These and other objects, features and advantages of the disclosed technology will become more apparent upon reading the following specification in conjunction with the accompanying figures and examples.

DETAILED DESCRIPTION

Figure 1:
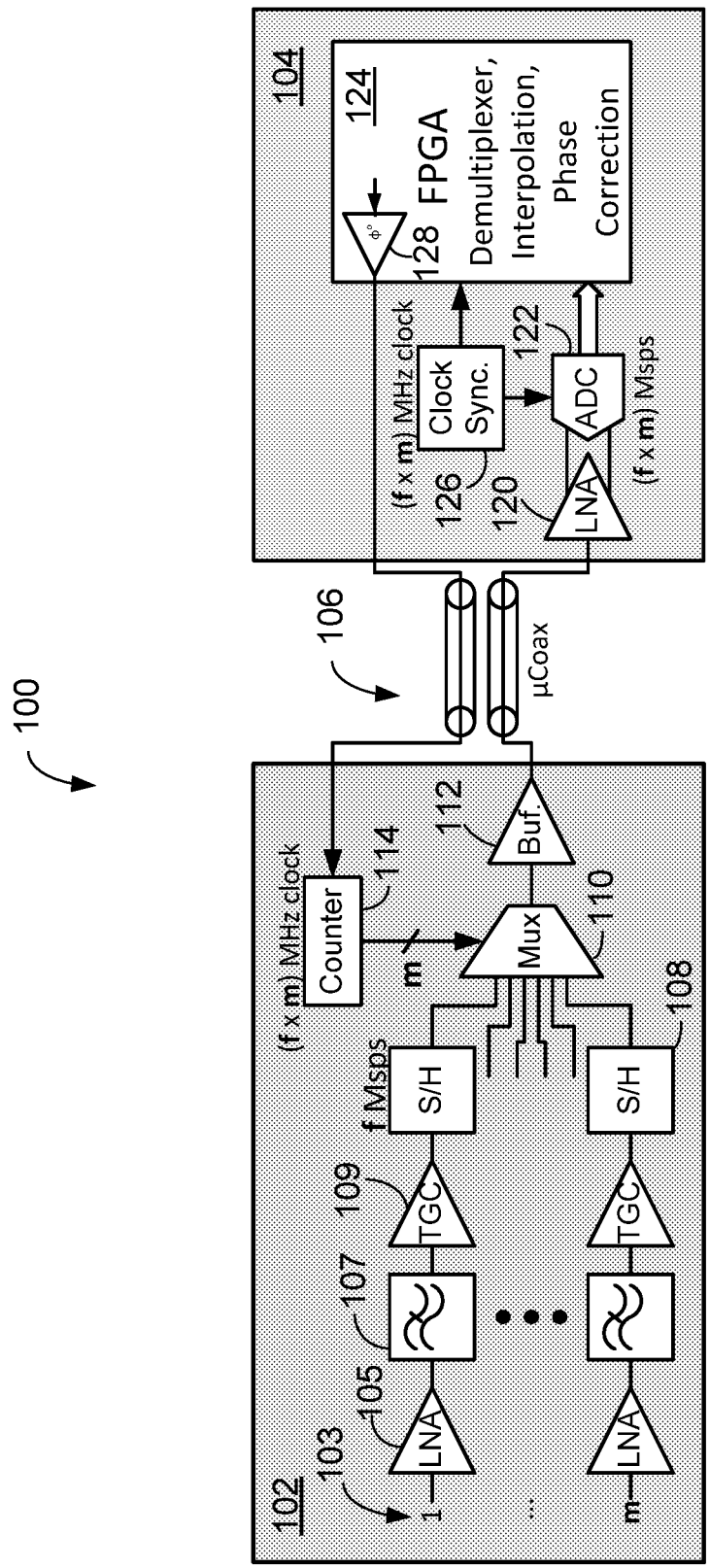
FIG. 1 depicts an analog time-division multiplexing (TDM) system 100 using digital demultiplexing, in accordance with an example implementation of the disclosed technology.

Certain embodiments of the disclosed technology relate to systems, methods, and devices for reduction of cabling and associated electrical connections associated with the imaging catheters. Certain example implementations of the disclosed technology can apply to catheters (and/or other imaging probes) that utilize piezoelectric micromachined ultrasound transducer (PMUT), capacitive micromachined ultrasonic transducer (CMUT), conventional bulk piezoelectric material based transducers and the like, as a reduction in the cable count may enable the manufacturing and use of size-restricted probes.

As described herein, certain systems and methods are disclosed for using time division multiplexing (TDM) with CMUT-on-CMOS-based catheters. However, the disclosed technology may be applied for cable reduction and/or system complexity reduction for any type of ultrasound probe, including but not limited to 1-D or 2-D transducer array using bulk piezoelectric, PMUTs, single chip or multi-chip integrated CMUTs, and CMOS electronics. For example, by utilizing a 16×1 TDM scheme for a 192 element 1-D array, the cable count on the receiver side can be reduced to 12. In another example, certain systems and methods disclosed herein may be applied to the external receiver end of the system to reduce the number of analog-to-digital converters (ADCs) in the system.

As disclosed herein, certain TDM and digital demultiplexing schemes may be utilized for an intracardiac imaging system. In an example implementation, the system may operate in the 4-11 MHz range. An example system is disclosed in which a TDM integrated circuit (IC) with 8×1 multiplexer is interfaced with a fast ADC to transmit a signal through a reduced cable (micro-coaxial catheter cable bundle). In an example implementation, the received signal may be processed with an FPGA to recover the signals.

Certain example implementations of the disclosed technology are discussed in "Time-Division Multiplexing for Cable Reduction in Ultrasound Imaging Catheters," T. M. Carpenter, M. W. Rashid, M. Ghovanloo, D. Cowell, S. Freear, and F. Levent Degertekin; Biomedical Circuits and Systems Conference (BioCAS), 22 Oct. 2015 IEEE, pp. 1-4, the contents of which are incorporated herein by reference as if presented in full.

Additional example implementations of the disclosed technology are discussed in "Direct Digital Demultiplexing of Analog TDM Signals for Cable Reduction in Ultrasound Imaging Catheters," Thomas M Carpenter, M Wasequr Rashid, Maysam Ghovanloo, David M J Cowell, Steven Freear, and F Levent Degertekin; IEEE Transactions on Ultrasonics, Ferroelectrics, and Frequency Control, 21 Aug. 2016; 63(8): pp. 1078-85, 22 Apr. 2016, the contents of which are incorporated herein by reference as if presented in full.

Certain example implementations of the disclosed technology may be applied in, or used in conjunction with sub-aperture beamforming (and/or µ-beamforming) applications. For example, a catheter probe may include an array of transducer elements. The array may include a plurality of groups of transducer elements, with each group including plurality of transducer elements arranged in a two-dimensional array. In accordance with an example implementation of the disclosed technology, each transducer element may be capable of converting an image signal from acoustic form to electrical form. In certain example implementations, the probe may further include a processor for controlling relative intragroup phasings between respective image signals corresponding to the elements of a group, and such image signals may be phased and combined into a group signal. In an example implementation, the processor may generate a plurality of group signals corresponding to the respective plural groups. In an example implementation, once the group signals are generated, they may be transmitted using the TDM techniques disclosed herein.

Another example implementation of the disclosed technology may be applied as a secondary cable count reduction method, for example, after beamforming is performed on a 2-D array to reduce the channel count. For example, an 8×1 TDM may be utilized after beamforming with 9 element groups over the array to yield a 72×1 reduction in cable count (as compared to the array elements). Such reduction in cable count may be beneficial for reduced-size catheter application such as 3D transesophageal echocardiography (TEE). For example, the disclosed technology may provide certain improvements for use with applications that utilize phased arrays of piezoelectric transducers for beamforming and electronic volume scanning, such as described in "A volumetric CMUT-based ultrasound imaging system simulator with integrated reception and µ-beamforming electronics models," G. Matrone A. S. Savoia M. Terenzi G. Caliano F. Quaglia and G. Magenes, IEEE Transactions on Ultrasonics, Ferroelectrics, and Frequency Control, vol. 61 no. 5 pp. 792-804 May 2014, the contents of which are incorporated by reference in their entirety as if fully set forth herein.

Certain aspects of the disclosed technology may also provide certain improvements over U.S. Pat. No. 5,229,933 to D. Larson, III, entitled "2-D phased array ultrasound imaging system with distributed phasing," Jul. 20, 1993. the contents of which are incorporated by reference in their entirety as if fully set forth herein Certain application of the disclosed technology may provide improvements over similar CMUT imaging systems, for example, as discussed in "Two Approaches to Electronically Scanned 3D Imaging Using cMUTs," C. Daft, S. Panda, P. Wagner, and I. Ladabaum, Ultrasonics Symposium, 2006, IEEE, 1 Oct. 2006, pp. 685-688. Certain application of the disclosed technology may also provide improvements over similar CMUT imaging systems as discussed in U.S. Pat. Nos. 7,679,263 and 7,824,338 to Daft, et al. For example, the disclosed technology provides systems and methods that can be used to measure signal delays, determine optimum sampling times, and adjust clock phase to adjust the sampling position.

In another example implementation of the disclosed technology, CMUT-on-CMOS with on-chip multiplexing can be utilized to reduce a number of electrical connections that may otherwise be required in traditional approaches. Certain example implementations may utilize analogue TDM to sample multiple CMUT elements continuously, for example, to increase the frame rate of the system and to reduce motion artefacts by simultaneous collection of reflection data from the transducers. Certain example embodiments of the disclosed technology will be described more fully hereinafter with reference to the accompanying drawings, in which certain example embodiments are disclosed.

FIG. 1 depicts an analog time-division multiplexing (TDM) system 100 using digital demultiplexing, in accordance with an example implementation of the disclosed technology. In this example implementation, the system 100 can include a transmitter 102 and a receiver 104 connected by pcoax cables 106 (not to scale). The transmitter 102, for example, may be located at the tip of a catheter.

As depicted in FIG. 1, the transmitter 102, may include m number of channels 103. In one example implementation, each channel 103 may be in communication with a respective imaging transducer element. In another example implementation, an individual channel 103 may be in communication with a plurality of imaging transducer elements, for example, after the respective signals from the plurality of imaging transducer elements are combined by micro beam forming or sub aperture processing.

In certain example implementations, each of the m channels 103 may include one or more of: a low noise amplifier (LNA) 105, anti-aliasing filtering circuitry 107, and time gain control circuitry 109. FIG. 1 depicts the anti-aliasing filtering circuitry 107 before the time gain control circuitry 109, however, in certain example implementations, the order may be swapped, for example, by placing the time gain control circuitry 109 before the anti-aliasing filtering circuitry 107.

According to an example implementation of the disclosed technology, each LNA 105 may be configured with a high input impedance, and may amplify the signal received from a corresponding channel 103. The anti-aliasing filter circuitry 107 may be utilized to reduce or eliminate any frequency components of the signal and noise that are above a Nyquist frequency of the system 100, which may be determined by the clock frequency. In an example implementation, the time gain control circuitry 109 may be utilized to increase the gain of a received pulse, for example, to compensate for attenuation of a pulse as it travels through the body.

In certain example implementations, the transmitter 102 may include series of sample and hold ("S/H") buffers 108 (one per element), an analogue multiplexer 110, a cable driver/buffer 112, and sequencing logic, including, but limited to a counter 114.

In accordance with an example implementation of the disclosed technology, the receiver 104 may be connected to the transmitter 102 via pcoax cables 106, and may be separated from the transmitter 102 from about one to several meters. The separation or length of the pcoax cables 106 may be configured based on requirements, such as a minimum separation to reduce RF noise from nearby MRI or other equipment. According to an example implementation of the disclosed technology, the receiver 104 may include a low noise amplifier (LNA) 120 and a synchronised analog-to-digital converter (ADC) 122 which buffers then performs quantisation of the samples, followed by a field programmable gate array (FPGA) 124 which may perform demultiplexing in the digital domain.

In accordance with an example implementation of the disclosed technology, the transmitter 102 may sample the signals from each channel 103 simultaneously and then multiplex this signal for transmission through the cable 106. The resulting transmitted TDM signal may take the form of a discreet time pulse-amplitude modulated (PAM) signal in which the amplitude has a continuous (analogue) range of voltages.

According to an example implementation, once the signal is sent to the receiver 104, the signal's amplitude may be quantised and converted into a digital stream of data. The digital data may then be de-multiplexed by splitting the samples into multiple streams which can then be individually interpolated and filtered using DSP techniques.

Figure 2:
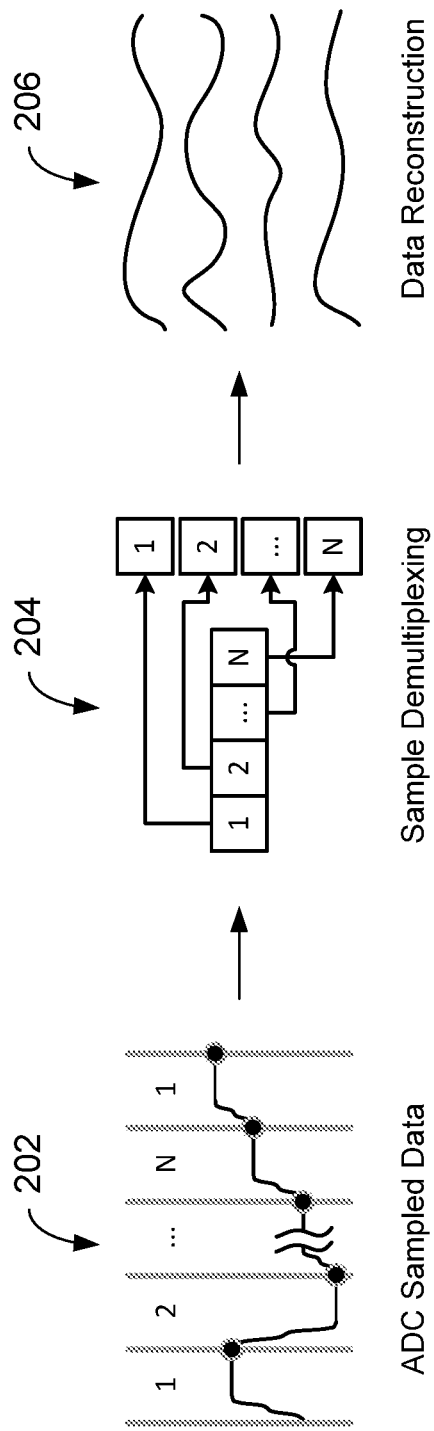
FIG. 2 depicts sampling, multiplexing, and data reconstruction of a sampled data stream, according to an example implementation of the disclosed technology.

FIG. 2 depicts an example process in which the received (multiplexed) data may be sampled 202, demultiplexed 204, and reconstructed 206 channel-by-channel, with each reconstructed signal corresponding to the respective imaging transducer element. For example, the receiver (such as the receiver 104 in FIG. 1) may include a clock synchronized analog-to-digital converter (such as ADC 122 in the receiver 104 of FIG. 1) for sampling 202 the received multiplexed data. According to an example implementation of the disclosed technology, the ADC sampled data may be buffered and demultiplexed 204. In accordance with an example implementation of the disclosed technology, the demultiplexed 204 data may then be utilized to reconstruct 206 the signals that correspond to the respective imaging transducer elements.

As may be appreciated by those having skill in the art, the system and process as depicted in FIGS. 1 and 2 provides certain enabling technology to deliver the TDM signal (which can include signals from multiple transducer elements) through a single (or reduced count) physical cable 106, thereby reducing the count and associated bulk and diameter of the cable bundle.

In an example implementation, the physical channel in which the TDM signal is transmitted (for example, the pcoax cable 106 in the catheter) requires sufficient bandwidth to carry the multiplexed signal, and this required bandwidth may be much greater than the of an individual CMUT device as multiple elements are multiplexed together. In an example implementation, the required bandwidth for the physical channel may be determined as a function of the sample rate times the number of transducer elements. In certain example implementations, additional bandwidth margin may be needed to allow each TDM period to have settled at a constant level before the sample is taken. According to an example implementation of the disclosed technology, and to allow settling, the required bandwidth for the physical channel may be to be roughly 3 to 4 times the total ADC sample rate. In one example implementation, the ADC may not include any anti-aliasing filtering, as such filtering would reduce the channel bandwidth. Certain example implementations of the disclosed technology may intentionally utilize aliasing in the ADC to remove the carrier signal.

Referring again to FIG. 1, and according to an example implementation of the disclosed technology, the conversion of the TDM signal by the ADC 122 is synchronised with the sample and hold circuitry 108 and the multiplexer 110 by the clock 126 with phase correction 128. The synchronisation may be performed for two purposes: first, to ensure that each quantisation performed for the next channel by the ADC 122 is done such that in each loop of the TDM counter there is exactly one sample taken for every channel; and second, the phase correction 128 may ensure that quantisation is performed in the center of each TDM period so that a true representation of the sample is generated. For example, since electrical signals have a finite propagation speed, and since cable length may vary from catheter to catheter, the phase of the ADC clock 126 and TDM counter 114 can differ between catheters. Without the phase alignment (for example, via the phase correction 128) the sampling could be done at the wrong time, such as during the dead time between channels or during a rise/fall period in the cable before settling. Thus, in certain example implementations, link training may be performed to set the proper phase correction 128 alignment for a given catheter cable length. In an example implementation, the link training may utilize a sequence to determine if the optimal alignment has been achieved or if the clock phases need to be adjusted. Once the alignment is complete, any process-related and/or temperature-related variations of phase delays in the system may be accounted for.

In accordance with an example implementation of the disclosed technology, the same clock 126 may be utilized for both the TDM sequencing/sampling logic (for example, in the transmitter 102) as is used for the ADC (for example, in the receiver 104) to provide synchronous clocking and to avoid beat frequencies. In other example implementations, two synchronous clocks of different frequencies may be utilized.

Example Hardware Implementation and Testing

Certain example implementations and associated test results of the disclosed technology have been published in a conference paper entitle: "Time-division multiplexing for cable reduction in ultrasound imaging catheters," Biomedical Circuits and Systems Conference (BioCAS), 2015 IEEE, 22 Oct. 2015, by Thomas M. Carpenter, M. Wasequr Rashid, Maysam Ghovanloo, D. Cowell, S. Freear, and F. Levent Degertekin. The entire contents of this publication are incorporated herein, as if presented in full. This publication describes an example implementation of the disclosed technology that was constructed utilizing silicon hardware for testing the viability of the disclosed technology.

In an initial test system, a waveform generator was utilized for outputting simulation data corresponding to 0.18 μm high speed process design, which showed promising results and confirmed the TDM approach as a viable solution. A subsequent design was manufactured using a 0.35 μm process and the hardware was tested to further confirm the viability of the approach.

Figure 3:
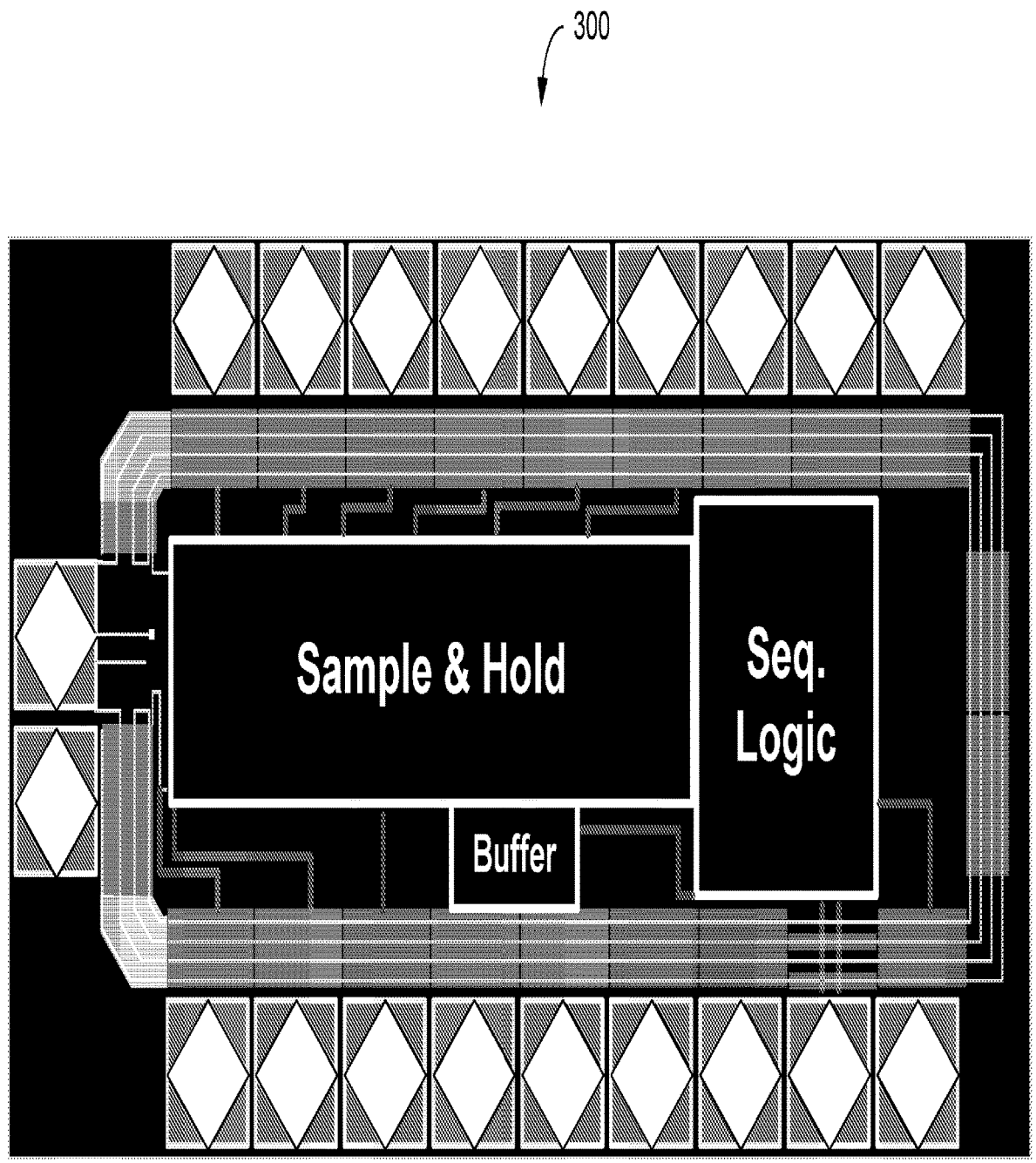
FIG. 3 shows an image of a silicon integrated circuit 300 for the TDM transmitter circuitry, according to an example implementation of the disclosed technology.

FIG. 3 is an image of a silicon IC 300 that was manufactured and utilized for testing the TDM transmitter circuitry. The IC 300 includes sample and hold circuitry, an analogue multiplexer with a link training generator, a high frequency buffer, and sequencing logic. Certain aspects of the IC 300 and associated example implementations will be discussed below with reference to the block diagram 400 of FIG. 4, which depicts TDM multiplexer sequencing logic with link training capabilities, according to an example implementation of the disclosed technology.

Example Clocking Scheme

In accordance with an example implementation of the disclosed technology, different clocking schemes may be utilized for synchronising the TDM process (as performed at the transmitter 102 of FIG. 1, for example) and ADC process (as performed at the receiver 104 of FIG. 1, for example). In a first example implementation, and as depicted in FIG. 1, both the "TDM clock" and "ADC clock" may be sourced or derived from the same oscillator and run at full frequency fxm [MHz], where f is the sample rate per channel and m is the number of channels in the transmitter for which TDM is applied. Since both clock sources originate from the same oscillator, this embodiment may include a minimal amount of clock circuitry in the transmitter 102, such as a buffer 112 near the tip of the catheter. Although the crosstalk between clock and analogue signals may be higher than in other schemes (due to a higher frequency), such crosstalk may match the ADC frequency and may be intentionally aliased to a DC component where it may be easily removed, for example, by a low pass filter. This embodiment, however, may include CMOS electronics that are capable of running at high frequency. For example, a 25 MSPS system with 8 channels may include circuitry capable of at least 200 MHz. Test results from the prototype TDM multiplexer indicate that such frequency operation is possible, even utilizing the slower 0.35 μm IC manufacturing process.

In another example implementation, a TDM clock (for example, the clock source utilized for driving the sampling and multiplexing at the transmitter 102) may be run at half of the frequency of the ADC clock. In this example implementation, all of the TDM sequencing logic and counters may be configured as dual-edge flip flops. Based on this configuration, a sample may be taken on each clock edge to achieve a sample rate at the ADC clock. However, this embodiment may require a clock with exactly 50% duty cycle to ensure the correct sample time. Furthermore, any crosstalk could affect each sample differently and may not be removed through aliasing. One advantage of this embodiment, however, is that running the "TDM clock" at half the frequency of "ADC clock" could reduce power consumption due to a lower switching rate, which may prove advantageous in certain applications.

In yet another example implementation, a Delay-Locked Loop (DLL) may be implemented in the CMOS circuitry. In this implementation, a relatively slow clock may be utilized and may help reduce crosstalk levels as the clock could be slowed enough that each clock edge transition would occur after multiplexing the "m" previous inputs from the transducer elements. In this way, crosstalk from the clock could be removed entirely. In certain example implementations, the DLL may allow clock generation that can be phase synchronous to the reference clock and can be phase shifted either by adjusting the reference clock, or the DLL itself (via a digital control signal). In this example implementation, synchronisation and phase alignment requirements may be achieved with reduced power consumption.

Example Training Scheme

In accordance with an example implementation of the disclosed technology, link training may be utilized in the TDM process. One example of such training implementation is depicted in the block diagram 400 of FIG. 4, which depicts TDM multiplexer sequencing logic having link training capabilities. Certain example implementations of the training, as discussed with reference to FIG. 4 may be included as part of the TDM system 100 of FIG. 1, for example, to detect sampling delays of the ADC to correctly align the ADC and TDM clocks to ensure a correct sample is taken.

In certain example implementations, phase delays caused by signal propagation through the transmitter circuitry, catheter cabling, etc. may be detected and an alignment process may be utilized to compensate for the various delays. In one example implementation, the alignment process may be initiated by placing the transmitter 102 into a training mode, for example, by enabling a link training mode select 402.

In accordance with an example implementation of the disclosed technology, the phase detection may include two stages: (1) sampling the delays caused by the ADC; and (2) determining delays caused by other components of system (such as cabling, etc.). For example, a training mode 402 may be selected to disconnect the analogue inputs to the multiplexer 110 while allowing the multiplexer sequencing logic to run. In an example implementation, each input to the multiplexer 110 may be fixed to one of two bias rails, which may result in a known signal being produced at the output of the multiplexer 110. Such an approach may provide phase alignment requirements that may allow pulse extraction, control aliasing, and/or reduce distortion in the recovered signal.

Figure 4:
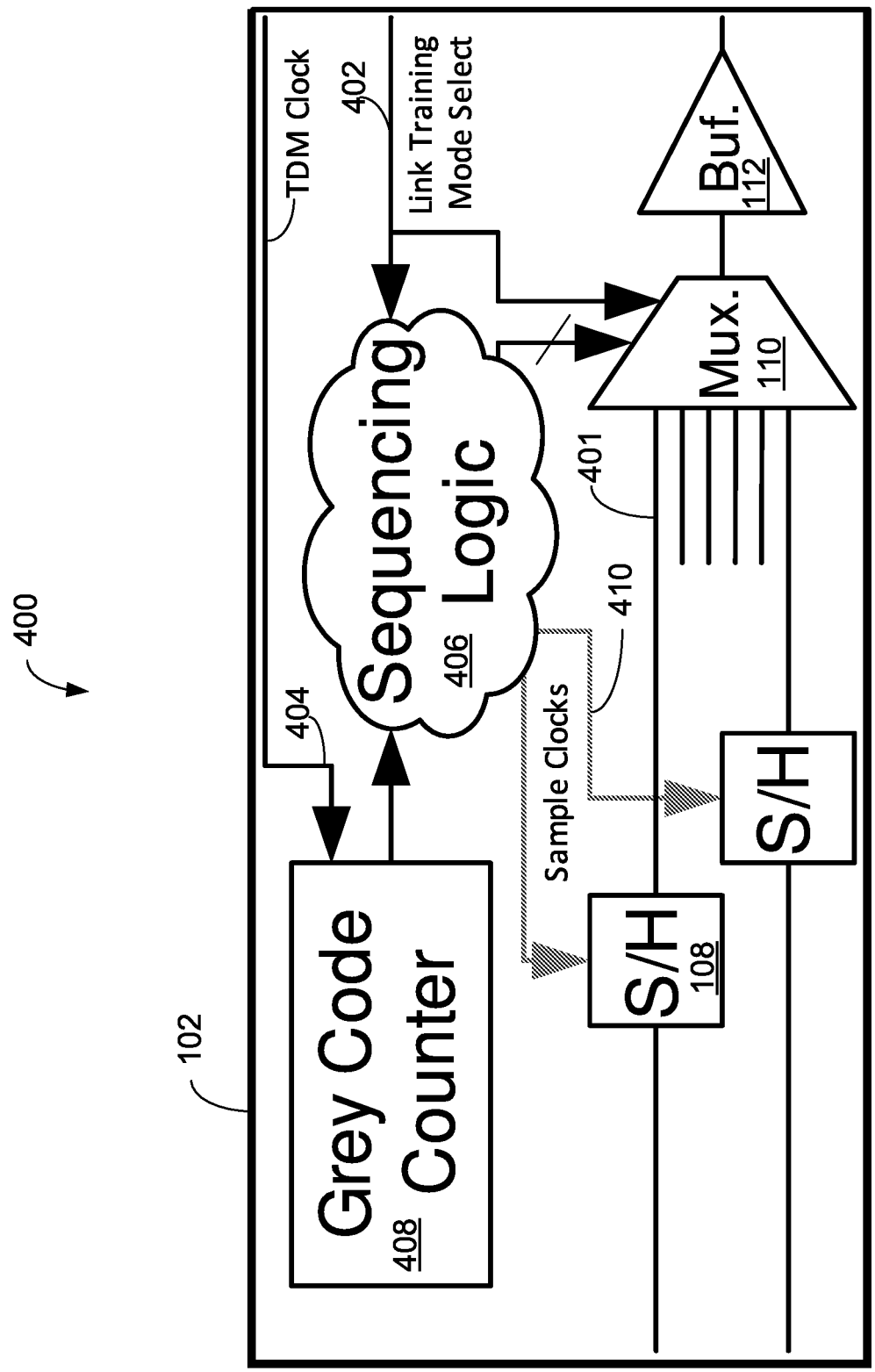
FIG. 4 depicts a block diagram 400 of a TDM multiplexer sequencing logic with link training capabilities, according to an example implementation of the disclosed technology.

In an example implementation, and as depicted in FIG. 4, a first channel 401 may be fixed to one bias rail (for example, VCC) and all other channels may be connected to a second rail (for example, ground, or another distinguishable rail). By analysing the converted data the first channel 401 having the first bias may be identified by its quantised code differing from other channels attached to the second rail. The selection and unique biasing of the first channel 401 is described here for simplicity, but in practice it doesn't matter which channel is utilized as long as both the transmitter 102 and receiver 104 ends use the same one.

Figure 5A:
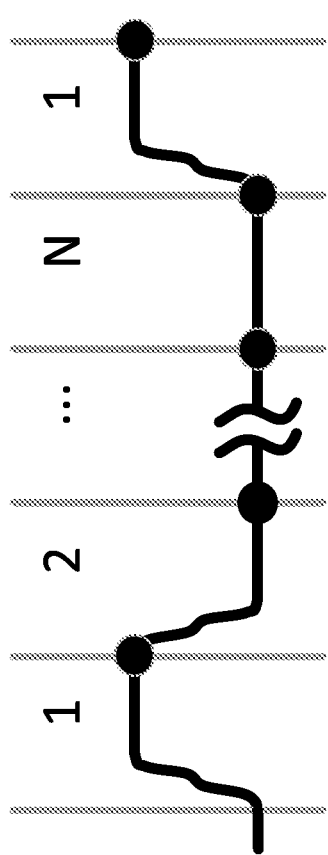
FIG. 5(a) depicts training sequence to identify a particular channel, according to an example implementation of the disclosed technology.

FIG. 5(a) depicts a training sequence, as described above with reference to FIG. 4, in which a first channel is activated by fixing it to one bias rail, and the remaining channels 2-N are distinguishable by fixing them to another bias rail. Certain example implementations of this approach may be utilized to identify, analyze, and compensate a particular channel.

Figure 5B:
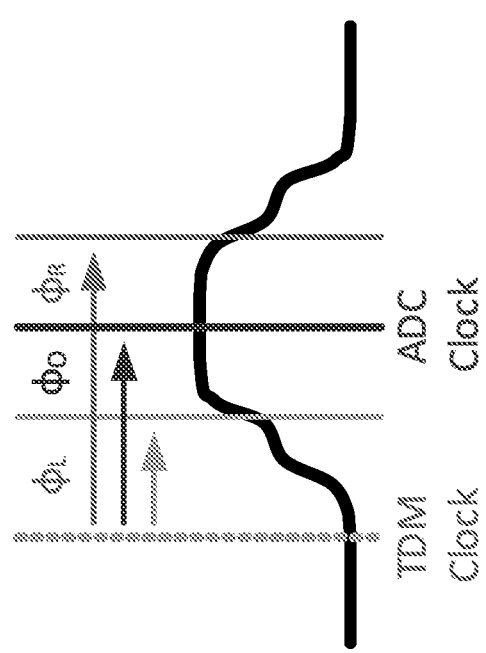
FIG. 5(b) depicts an example technique for locating an optimal phase between TDM and sample clocks, for example, to avoid sampling during channel switching transient, in accordance with an example implementation of the disclosed technology.

FIG. 5(b) depicts an example technique for locating an optimal phase between TDM and sample clocks, for example, to avoid sampling during channel switching transient. For example, once the activated channel is identified, the TDM clock phase can be adjusted determine the optimum alignment. By locating the phases where the quantised value of the activated channel begins to bleed into the other channels (i.e. the rising and falling edge of the pulse), the phases $\varphi_L$ and $\varphi_R$ can be identified. In accordance with an example implementation of the disclosed technology, the optimal phase $\varphi_O$ for performing the sampling can then be determined, for example, as the midpoint of these two phases $\varphi_L$ and $\varphi_R$. By locking in this phase shift, any propagation delays in the system may be fully accounted for and analogue data may be sent through the system. As known by those having skill in the art, the exact phase shifting method may depend on the clocking scheme being used.

Once the training mode has been completed (for example, to determine the various signal delays associated with the various signal paths, cable lengths, ADC delays, MUX delays, etc.), the subsequent phase corrections for each individual channel sampling (i.e., for setting the optimum sampling points) may be generated in the FPGA 124 and provided to the transmitter 102 via the phase corrected 128 clock signal, for example, to set delay-compensated sampling point in the sample and hold circuits 108.

Example Multiplexer Sequencing Logic

Referring again to FIG. 4, the transmitter 102 circuitry can include sequencing logic 406 to provide correct selection of channels and to perform sampling of each channel at the correct time (as discussed above). Certain example implementations of the transmitter 102 can include decoder circuitry can include a counter 408 to select each channel in turn (and may be resynchronised with the FPGA after reset) followed by additional logic 406 circuitry to generate the sample clocks 410 and multiplexer 110 selection signals with dead time generation. To prevent short circuits due to the switching time as one channel is disconnected and the next is connected, the dead time circuitry may be utilized to ensure that for a small period, no channel is connected.

Figure 6:
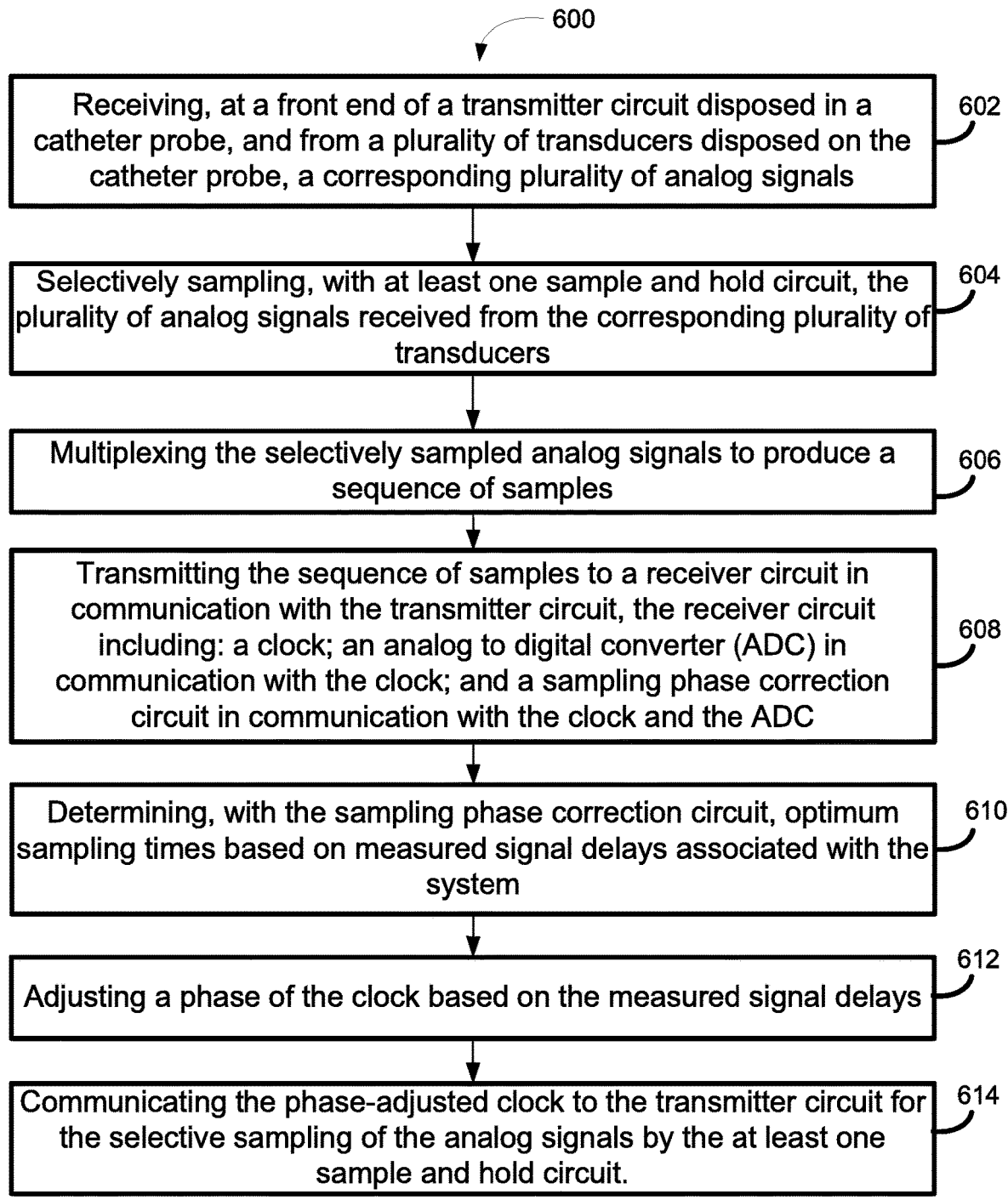
FIG. 6 is a flow diagram of a method 600, according to an example implementation of the disclosed technology.

FIG. 6 is a flow diagram of a method 600, according to an example implementation of the disclosed technology. In block 602, the method 600 includes receiving, at a front end of a transmitter circuit disposed in a catheter probe, and from a plurality of transducers disposed on the catheter probe, a corresponding plurality of analog signals. In block 604, the method 600 includes selectively sampling, with at least one sample and hold circuit, the plurality of analog signals received from the corresponding plurality of transducers. In block 606, the method 600 includes multiplexing the selectively sampled analog signals to produce a sequence of samples. In block 608, the method 600 includes transmitting the sequence of samples to a receiver circuit in communication with the transmitter circuit, the receiver circuit including: a clock; an analog to digital converter (ADC) in communication with the clock; and a sampling phase correction circuit in communication with the clock and the ADC. In block 610, the method 600 includes determining, with the sampling phase correction circuit, optimum sampling times based on measured signal delays associated with the system. In block 612, the method 600 includes adjusting a phase of the clock based on the measured signal delays. In block 614, the method 600 includes communicating the phase-adjusted clock to the transmitter circuit for the selective sampling of the analog signals by the at least one sample and hold circuit.

As discussed herein, the multiplexing is operable to reduce a number of cables connecting the transmitter circuit to the receiver circuit.

Certain example implementations include matching an input impedance of the receiver circuit with a characteristic impedance of a coaxial cable connecting the receiver circuit to the transmitter circuit.

Certain example implementations include training one or more of the transmitter circuit and the receiver circuit based on determining delays associated with each of the plurality of analog signals in sequence of samples.

Example implementations of the disclosed technology include conditioning the received plurality of analog signals with one or more of: a low noise amplifier; an anti-aliasing filter; and/or a time gain controller.

In certain example implementations, the beamforming can include controlling relative phases between respective signals of a group of transducer elements from the plurality of transducers. Certain example implementations of the beamforming can further include combining the respective phased signals for sampling by the at least one sample and hold circuit. In certain example implementations, controlling the relative phases includes controlling intragroup phasings between the respective signals.

Figure 7:
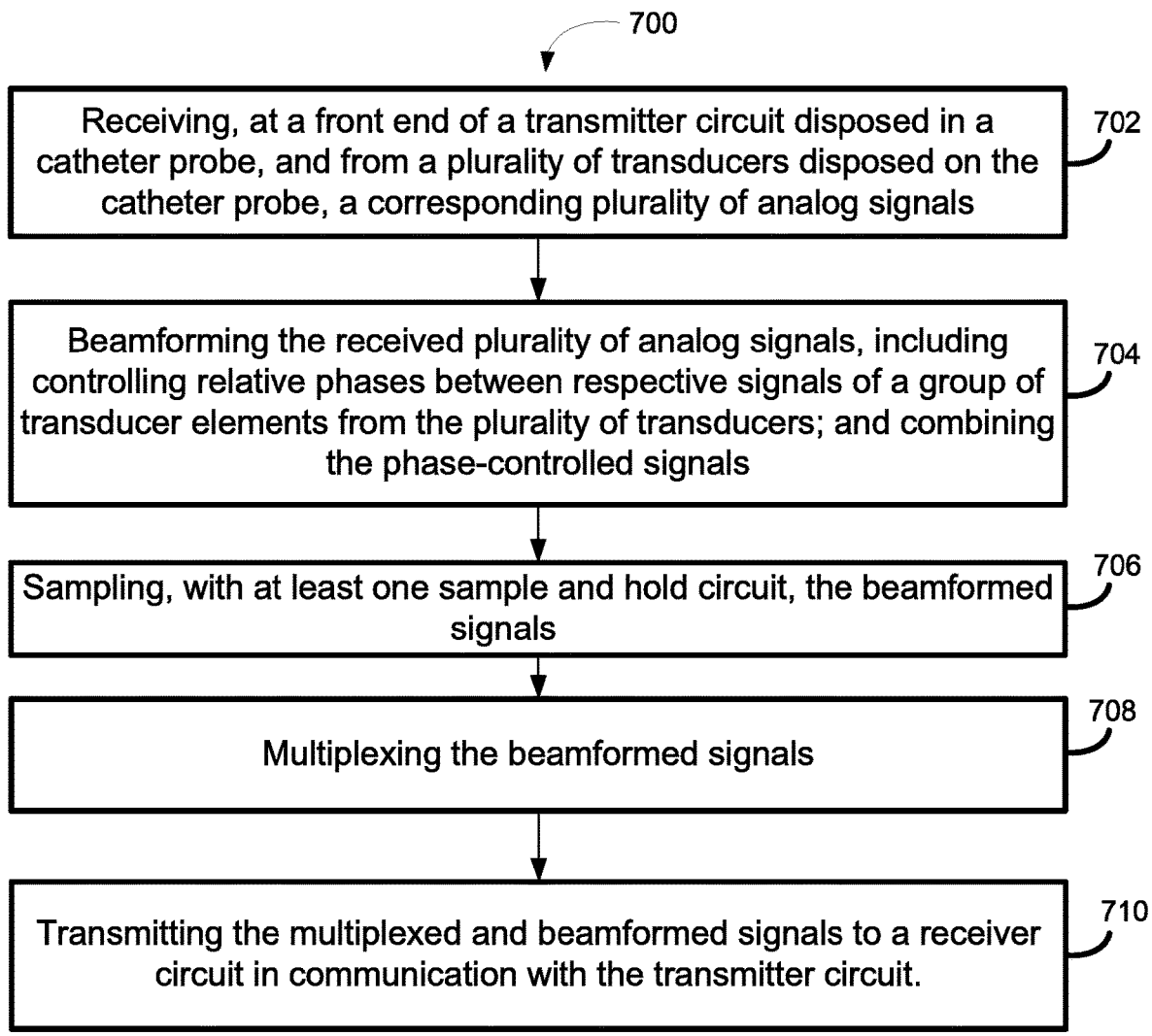
FIG. 7 is another flow diagram of a method 700, according to an example implementation of the disclosed technology.

FIG. 7 is a flow diagram of a method 700, according to an example implementation of the disclosed technology. In block 702, the method 700 includes receiving, at a front end of a transmitter circuit disposed in a catheter probe, and from a plurality of transducers disposed on the catheter probe, a corresponding plurality of analog signals. In block 704, the method 700 includes beamforming the received plurality of analog signals, including controlling relative phases between respective signals of a group of transducer elements from the plurality of transducers; and combining the phase-controlled signals. In block 706, the method 700 includes sampling, with at least one sample and hold circuit, the beamformed signals. In block 708, the method 700 includes multiplexing the beamformed signals. In block 710, the method 700 includes Transmitting the multiplexed and beamformed signals to a receiver circuit in communication with the transmitter circuit.

Certain example implementations of the disclosed technology may include determining, with the receiver circuit, a phase adjustment. In an example implementation, the receiver circuit includes a clock; an analog to digital converter (ADC) in communication with the clock; and a sampling phase correction circuit in communication with the clock and the ADC. In certain embodiments, determining the phase adjustment is based at least in part on measured signal delays.

Some implementations can include adjusting a phase of the clock is based on the determined phase adjustment, and communicating the phase-adjusted clock to the transmitter circuit for selective sampling of the beamformed signals.

Certain example implementations include training one or more of the transmitter circuit and the receiver circuit based on determining delays associated with each of the beamformed signals.

Certain embodiments of the disclosed technology may include a system to perform one or more of the methods described above. The system can include an imaging array comprising a plurality of transducers disposed on at least a distal portion of a catheter probe, and a transmitter circuit disposed in the catheter probe. The transmitter circuit can include: a plurality of sample and hold circuits configured for selective sampling of analog signals received from the corresponding plurality of transducers; and a multiplexer in communication with the plurality of sample and hold circuits and configured for sequencing samples received from the plurality of sample and hold circuits. The system can include a receiver circuit in communication with the transmitter circuit. The receiver circuit may include: a clock; an analog to digital converter (ADC) in communication with the clock; and a sampling phase correction circuit in communication with the clock and the ADC. The sampling phase correction circuit is configured to: determine optimum sampling times based on measured signal delays associated with the system; adjust a phase of the clock based on the measured signal delays; and communicate the phase-adjusted clock to the transmitter circuit for the selective sampling of the analog signals by the plurality of sample and hold circuits.

In certain example implementations, the system can include one or more cables (such as coax or micro-coax) to connect the transmitter circuit and the receiver circuit. The one or more cables can include a first conductive path configured to communicate multiplexed and combined (and/or serialized and/or sequenced) transducer data from the transmitter circuit to the receiver circuit, and a second conductive path configured to communicate the phase-adjusted clock signal from the receiver circuit to the transmitter circuit.

Certain example implementations include a third conductive path configured to communicate a phase detection training enable signal from the receiver circuit to the transmitter circuit and to cause the system to determine delays associated with each of the plurality of analog signals.

According to an example implementation of the disclosed technology, the input impedance of the receiver circuit is matched to an impedance of the first conductive path.

According to an example implementation of the disclosed technology, the transmitter circuit can further include plurality of conditioning circuits in communication with the corresponding plurality of transducers, each of the plurality of conditioning circuits comprising one or more of: a low noise amplifier; an anti-aliasing filter; and/or a time gain controller.

In certain example implementations, the transmitter circuit further includes a counter in communication with the phase-adjusted clock and configured to advance the multiplexer.

In an example implementation, the receiver circuit includes a low noise amplifier in communication with a front end of the analog to digital converter.

According to an example implementation of the disclosed technology, the transmitter circuit includes selectable link training mode circuitry configured to determine delays associated with each channel of the system. In an example implementation, the sampling phase correction circuit is configured to determine the optimum sampling times based on the determined delays.

Certain example implementations include a beamforming processor configured to control relative phases between respective signals of a group of transducer elements. In an example implementation, the beamforming processor may be further configured to combine the respective phased signals for sampling by at least one of the plurality of sample and hold circuits In the description provided herein, numerous specific details are set forth. It is to be understood that certain embodiments may be practiced without each and every one of the specific details. In other instances, well-known methods, structures and techniques have not been shown in detail in order not to obscure an understanding of this description. The term "exemplary" herein is used synonymous with the term "example" and is not meant to indicate excellent or best. References to "one embodiment," "an embodiment," "exemplary embodiment," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the disclosed technology are intended to be illustrative and not restrictive. Many suitable materials that would perform the same or a similar function as the materials described herein are intended to be embraced within the scope of the disclosed technology. Such other materials not described herein can include, but are not limited to, for example, materials that are developed after the time of the development of the disclosed technology.

The technology disclosed herein may be embodied in many different forms and should not be construed as limited to the embodiments set forth herein; rather, these embodiments are provided so that this disclosure is thorough, complete, and conveys the scope of the disclosed technology to those skilled in the art.

We claim:

1. A system, comprising:
   an imaging array comprising a plurality of transducers disposed on at least a distal portion of a catheter probe;
   a transmitter circuit disposed in the catheter probe, the transmitter circuit comprising;
     a plurality of sample and hold circuits configured for selective sampling of analog signals received from;
     a multiplexer in communication with the plurality of sample and hold circuits and configured for sequencing samples received from the plurality of sample and hold circuits;
   a receiver circuit separated from and in communication with the transmitter circuit, the receiver circuit comprising:
     a clock;
     an analog to digital converter (ADC) in communication with the clock; and
     a sampling phase correction circuit in communication with the clock and the ADC, wherein the sampling phase correction circuit is configured to:
       determine optimum sampling times based on measured signal delays associated with the system;
       adjust a phase of the clock based on the measured signal delays;
       communicate the phase-adjusted clock signal to the transmitter circuit for the selective sampling of the analog signals by the plurality of sample and hold circuits; and
   a cable configured to connect the transmitter circuit and the receiver circuit.

2. The system of claim 1, wherein the cable comprises:
   a first conductive path configured to communicate multiplexed transducer data from the transmitter circuit to the receiver circuit; and
   a second conductive path configured to communicate the phase-adjusted clock signal from the receiver circuit to the transmitter circuit.

3. The system of claim 2, further comprising a third conductive path configured to communicate a phase detection training enable signal from the receiver circuit to the transmitter circuit and to cause the system to determine delays associated with each of the analog signals.

4. The system of claim 2, wherein an input impedance of the receiver circuit is matched to an impedance of the first conductive path.

5. The system of claim 2, wherein at least the first conductive path comprises a micro-coaxial cable.

6. The system of claim 1, wherein the transmitter circuit further comprises a plurality of conditioning circuits in communication with the corresponding plurality of transducers, each of the plurality of conditioning circuits comprising one or more of:
   a low noise amplifier;
   an anti-aliasing filter; and
   a time gain controller.

7. The system of claim 1, wherein the transmitter circuit further comprises a counter in communication with the phase-adjusted clock signal and configured to advance the multiplexer.

8. The system of claim 1, wherein the transducers comprise ultrasonic transducers.

9. The system of claim 1, wherein the transducers comprise capacitive micromachined ultrasonic transducer (CMUT).

10. The system of claim 1, wherein the transducers comprise piezoelectric micromachined ultrasound transducers (PMUT).

11. The system of claim 1, wherein the receiver circuit further comprises a low noise amplifier in communication with a front end of the analog to digital converter.

12. The system of claim 1, wherein the transmitter circuit comprises selectable link training mode circuitry configured to determine delays associated with each channel of the system, and wherein the a sampling phase correction circuit is configured to determine the optimum sampling times based on the determined delays.

13. The system of claim 1, further comprising a beamforming processor configured to control relative phases between respective signals of a group of transducer elements, the beamforming processor further configured to combine the respective phase adjusted signals for sampling by at least one of the plurality of sample and hold circuits.

14. A method, comprising:
   receiving, at a front end of a transmitter circuit disposed in a catheter probe, and from a plurality of transducers disposed on the catheter probe, a corresponding plurality of analog signals;
   selectively sampling, with at least one sample and hold circuit, the plurality of analog signals received from the corresponding plurality of transducers;
   multiplexing the selectively sampled analog signals to produce a sequence of samples;
   transmitting the sequence of samples to a separate receiver circuit in communication with the transmitter circuit via a cable, the receiver circuit comprising:
     a clock;
     an analog to digital converter (ADC) in communication with the clock; and
     a sampling phase correction circuit in communication with the clock and the ADC;
   determining, with the sampling phase correction circuit, optimum sampling times based on measured signal delays;
   adjusting a phase of the clock based on the measured signal delays; and
   communicating the phase-adjusted clock signal to the transmitter circuit for the selective sampling of the analog signals by the at least one sample and hold circuit.

15. The method of claim 14, wherein the multiplexing is operable to reduce a number of conductors connecting the transmitter circuit to the receiver circuit.

16. The method of claim 14, further comprising matching an input impedance of the receiver circuit with a characteristic impedance of a coaxial cable connecting the receiver circuit to the transmitter circuit.

17. The method of claim 14, further comprising training one or more of the transmitter circuit and the receiver circuit based on determining delays associated with each of the plurality of analog signals in sequence of samples.

18. The method of claim 14, further comprising conditioning the received corresponding plurality of analog signals with one or more of:
- a low noise amplifier;
- an anti-aliasing filter; and
- a time gain controller.

19. The method of claim 14, further comprising beamforming the received corresponding plurality of analog signals, wherein the beamforming comprises:
- controlling relative phases between respective signals of a group of transducer elements from the plurality of transducers; and
- combining the respective phase adjusted signals for sampling by the at least one sample and hold circuit.

20. The method of claim 19, wherein the controlling the relative phases comprises controlling intragroup phasings between the respective signals.

21. A method, comprising:
- receiving, at a front end of a transmitter circuit disposed in a catheter probe, and from a plurality of transducers disposed on the catheter probe, a corresponding plurality of analog signals;
- beamforming the received corresponding plurality of analog signals, wherein the beamforming comprises:
  - controlling relative phases between respective signals of a group of transducer elements from the plurality of transducers; and
  - combining the phase-controlled signals;
- sampling, with at least one sample and hold circuit, the beamformed signals;
- multiplexing the beamformed signals; and
- transmitting the beamformed and multiplexed signals to a separate receiver circuit in communication with the transmitter circuit via a cable.

22. The method of claim 21, further comprising:
- determining, with the receiver circuit, a phase adjustment, the receiver circuit comprising:
  - a clock;
  - an analog to digital converter (ADC) in communication with the clock; and
  - a sampling phase correction circuit in communication with the clock and the ADC;
- wherein determining the phase adjustment is based at least in part on measured signal delays.

23. The method of claim 22 further comprising:
- adjusting a phase of the clock based on the determined phase adjustment; and
- communicating the phase-adjusted clock signal to the transmitter circuit for selective sampling of the beamformed signals.

24. The method of claim 21, wherein the multiplexing is operable to reduce a number of conductors connecting the transmitter circuit to the receiver circuit.

25. The method of claim 21, further comprising matching an input impedance of the receiver circuit with a characteristic impedance of a coaxial cable connecting the receiver circuit to the transmitter circuit.

26. The method of claim 21, further comprising training one or more of the transmitter circuit and the receiver circuit based on determining delays associated with each of the beamformed signals.

27. The method of claim 21, further comprising conditioning the received corresponding plurality of analog signals with one or more of:
- a low noise amplifier;
- an anti-aliasing filter; and
- a time gain controller.

28. The method of claim 21, wherein the beamforming comprises controlling intragroup phasings between the respective signals.

* * * * *